US009754513B1

(12) United States Patent
Lavigueur et al.

(10) Patent No.: US 9,754,513 B1
(45) Date of Patent: Sep. 5, 2017

(54) APPARATUS FOR SIMULATING INSERTION OF AN ELONGATED INSTRUMENT INTO A STRUCTURE INCLUDING A PULLEY AND A PULLEY POSITION SENSING ARRANGEMENT

(71) Applicant: CAE HEALTHCARE CANADA INC., Saint-Laurent (CA)

(72) Inventors: Maxime Lavigueur, Saint-Laurent (CA); Alexandre Picard, Saint-Laurent (CA); Giuseppe Mallaci, Saint-Laurent (CA); Francois Caron, Saint-Laurent (CA)

(73) Assignee: CAE HEALTHCARE CANADA INC., Saint-Laurent (CA)

( * ) Notice: Subject to any disclaimer, the term of this patent is extended or adjusted under 35 U.S.C. 154(b) by 0 days.

(21) Appl. No.: 15/054,501

(22) Filed: Feb. 26, 2016

(30) Foreign Application Priority Data

Feb. 26, 2016 (CA) ...................................... 2921852

(51) Int. Cl.
*G09B 23/28* (2006.01)
*G09B 9/00* (2006.01)
(Continued)

(52) U.S. Cl.
CPC ............ *G09B 23/285* (2013.01); *A61B 1/018* (2013.01); *A61B 34/76* (2016.02); *G09B 9/00* (2013.01); *G09B 23/28* (2013.01)

(58) Field of Classification Search
USPC ................................................ 434/262, 267
See application file for complete search history.

(56) References Cited

U.S. PATENT DOCUMENTS 5,431,645 A * 7/1995 Smith ................ A61B 18/1445
600/106
5,623,582 A * 4/1997 Rosenberg ............. B25J 9/1689
345/161
(Continued)

FOREIGN PATENT DOCUMENTS

CN 101653356 B 2/2010
CN 102855799 A 1/2013
(Continued)

*Primary Examiner* — Sam Yao
*Assistant Examiner* — William Ermlick
(74) *Attorney, Agent, or Firm* — IP Delta Plus Inc.

(57) ABSTRACT

The present disclosure relates to an apparatus for simulating insertion of an inner elongated instrument attached to a tether into a structure through an outer elongated instrument. The apparatus has a carriage for mounting the outer elongated instrument, for translation according to a translation of the outer elongated instrument. The apparatus has a pulley for anchoring a tether and rotating according to a longitudinal translation of the tether into the outer elongated instrument. The apparatus has a feedback force actuator for applying an adjustable resistive force to a translation of the carriage according to the sensed longitudinal position of the carriage and resistance characteristics of the structure, and for further applying an adjustable resistive force to a rotation of the pulley according to the sensed angular position of the pulley and the resistance characteristics. The present disclosure also relates to a medical insertion simulator comprising such an apparatus.

8 Claims, 13 Drawing Sheets

(51) Int. Cl.
*A61B 34/00* (2016.01)
*A61B 1/018* (2006.01)

(56) References Cited

U.S. PATENT DOCUMENTS

| | | | | |
|---|---|---|---|---|
| 5,769,640 | A * | 6/1998 | Jacobus | B25J 9/1689 434/262 |
| 5,800,179 | A * | 9/1998 | Bailey | A61B 34/76 434/262 |
| 5,821,920 | A * | 10/1998 | Rosenberg | G05B 19/409 345/156 |
| 6,074,213 | A * | 6/2000 | Hon | G09B 23/28 434/262 |
| 6,096,004 | A * | 8/2000 | Meglan | A61B 34/75 604/95.01 |
| 6,106,301 | A * | 8/2000 | Merril | G09B 23/285 434/262 |
| 6,375,471 | B1 * | 4/2002 | Wendlandt | G09B 23/285 434/262 |
| 6,377,011 | B1 | 4/2002 | Ben-Ur | |
| 6,470,302 | B1 | 10/2002 | Cunningham et al. | |
| 6,538,634 | B1 | 3/2003 | Chui et al. | |
| 6,773,263 | B2 | 8/2004 | Nicholls et al. | |
| 6,926,531 | B2 | 8/2005 | Wallaker | |
| 6,929,481 | B1 | 8/2005 | Alexander et al. | |
| 7,455,523 | B2 * | 11/2008 | Hendrickson | G09B 23/285 434/262 |
| 7,520,749 | B2 * | 4/2009 | Ohlsson | G06F 3/016 434/262 |
| 7,806,696 | B2 * | 10/2010 | Alexander | G09B 23/285 434/262 |
| 7,815,436 | B2 * | 10/2010 | Cunningham | G09B 23/285 345/158 |
| 7,819,799 | B2 * | 10/2010 | Merril | A61B 1/018 600/104 |
| 8,480,406 | B2 * | 7/2013 | Alexander | G09B 23/285 434/262 |
| 8,485,829 | B2 * | 7/2013 | Cusano | G09B 23/285 345/156 |
| 2001/0055748 | A1 * | 12/2001 | Bailey | G09B 23/285 434/262 |
| 2002/0111635 | A1 * | 8/2002 | Jensen | B25J 3/04 606/130 |
| 2004/0048230 | A1 * | 3/2004 | Alexander | G09B 23/285 434/262 |
| 2004/0076940 | A1 * | 4/2004 | Alexander | G09B 23/285 434/262 |
| 2005/0069854 | A1 | 3/2005 | Maier | |
| 2006/0127864 | A1 * | 6/2006 | Ohlsson | G06F 3/016 434/219 |
| 2006/0234195 | A1 * | 10/2006 | Grund-Pedersen | G09B 23/28 434/262 |
| 2007/0063971 | A1 * | 3/2007 | Vecerina | G09B 23/285 345/156 |
| 2007/0103437 | A1 * | 5/2007 | Rosenberg | G09B 23/285 345/161 |
| 2008/0126041 | A1 * | 5/2008 | Maspoli | A61B 34/76 703/7 |
| 2009/0130643 | A1 * | 5/2009 | Cusano | G09B 23/285 434/262 |
| 2011/0015483 | A1 * | 1/2011 | Barbagli | A61B 1/307 600/108 |
| 2011/0178508 | A1 * | 7/2011 | Ullrich | A61B 17/00234 606/1 |
| 2012/0178062 | A1 * | 7/2012 | Flaction | G09B 23/28 434/219 |
| 2015/0289946 | A1 * | 10/2015 | Johansson | G09B 23/285 434/262 |
| 2015/0325147 | A1 * | 11/2015 | Johansson | G09B 23/285 434/262 |
| 2016/0117956 | A1 * | 4/2016 | Larsson | G09B 23/285 434/262 |
| 2016/0166347 | A1 * | 6/2016 | Kishi | A61B 34/71 606/130 |

FOREIGN PATENT DOCUMENTS

| | | |
|---|---|---|
| CN | 103280145 A | 9/2013 |
| CN | 203373002 U | 1/2014 |
| CN | 203900980 U | 10/2014 |
| CN | 204965812 U | 1/2016 |
| EP | 1575015 A1 | 9/2005 |
| KR | 101372880 B1 | 3/2014 |
| WO | WO99/39315 | 8/1999 |
| WO | 2004015654 A1 | 2/2004 |
| WO | 2016005959 A1 | 1/2016 |

* cited by examiner

APPARATUS FOR SIMULATING INSERTION OF AN ELONGATED INSTRUMENT INTO A STRUCTURE INCLUDING A PULLEY AND A PULLEY POSITION SENSING ARRANGEMENT

TECHNICAL FIELD

The present invention generally relates to apparatuses for simulating insertion of an elongated instrument into a structure and medical insertion simulators for healthcare training.

BACKGROUND

Minimally invasive surgical procedures through the use of endoscopic instruments are more and more used for replacing conventional surgery. Indeed, technological progresses have provided miniaturized tools and implements that can be inserted through an endoscopic instrument in the body of a human for performing various tasks. These tools are generally combined with a video system to view from the inside the procedure being performed.

Virtual simulation systems have been developed for training medical professionals to perform these types of procedures. These simulation systems aim to produce realistic real-time simulated operating conditions for providing interactive training through the combination of real-time visual representation and interactive tactile force feedback returned to the medical professional under training.

The systems of the prior art are however complex, cumbersome and expensive. The haptic sensation returned to the trained medical professional is oftentimes not realistic enough. Moreover, such simulation systems often have to be used at a training center, as they are not designed to be easily transportable.

It would therefore be desirable to provide an improved simulation apparatus that would reduce at least one of the above-mentioned drawbacks of known simulation system.

SUMMARY

It is an object of the present invention to obviate or mitigate at least one disadvantage of previous simulation apparatus for simulating insertion of an elongated instrument into a structure.

It is another object to provide a portable simulation apparatus for simulating insertion of an elongated instrument into a structure that is transported in a conventional carry-on luggage.

It is another object of the invention to provide a simulation apparatus particularly adapted for simulation of transcatheter pacemaker implantation procedure.

Accordingly, there is provided an apparatus for simulating insertion of an inner elongated instrument attached to a tether into a structure through an outer elongated instrument. The apparatus comprises a casing having an aperture for receiving a distal end of the outer elongated instrument therethrough and a longitudinal guide fixedly mounted in the casing. The apparatus is provided with a carriage comprising a mounting plate for mounting the distal end of the outer elongated instrument, the carriage being slidably mounted onto the longitudinal guide for translation thereon according to a translation of the outer elongated instrument through the aperture of the casing. The apparatus also has a carriage position sensing element for sensing a longitudinal position of the carriage along the longitudinal guide. The apparatus further comprises a pulley having an outer tether receiving groove on a peripheral portion thereof and an anchoring element therein for anchoring a distal end of a tether extending through the outer elongated instrument, the pulley being rotatably mounted on the carriage for rotating according to a longitudinal translation of the tether into the outer elongated instrument. The apparatus is also provided with a pulley position sensing arrangement for sensing an angular position of the pulley representative of a relative longitudinal position of the inner elongated instrument attached to the tether. The apparatus also has a feedback force actuator mounted on the carriage and operatively connected to the casing for applying an adjustable resistive force to a translation of the carriage on the longitudinal guide according to the sensed longitudinal position of the carriage and resistance characteristics of the structure, the feedback force actuator being further connected to an axle of the pulley for applying an adjustable resistive force to a rotation of the pulley according to the sensed angular position of the pulley and the resistance characteristics of the structure.

According to another aspect, there is also provided a medical insertion simulator comprising an apparatus for simulating insertion of an inner elongated instrument attached to a tether into a structure through an outer elongated instrument. The medical insertion simulator is provided with an outer elongated instrument for attachment in the apparatus and a control unit for controlling the feedback force actuator. The medical insertion simulator further has a processing unit for receiving the sensed longitudinal position of the carriage, the sensed angular position of the pulley and a model of a patient's internal structure and associated resistance characteristics of the structure. The processing unit further determines the adjustable resistive force to apply to the translation of the carriage and the adjustable resistive force to apply to the rotation of the pulley according to previously received information for operating the control unit. The processing unit then further produces a visual display image of the patient's internal structure and movement of the inner and outer elongated instruments therein. The medical insertion simulator is further provided with a display unit for displaying the produced visual display image.

BRIEF DESCRIPTION OF THE DRAWINGS

Embodiments of the disclosure will be described by way of example only with reference to the accompanying drawings, in which.

DETAILED DESCRIPTION

The foregoing and other features will become more apparent upon reading of the following non-restrictive description of illustrative embodiments thereof, given by way of example only with reference to the accompanying drawings. Like numerals represent like features on the various drawings.

Various aspects of the present disclosure generally address one or more of the problems of simulating medical interventions relying on insertion of a medical instrument into an anatomical structure of a patient such as veins, arteries and other tubular anatomical structures. In the present description, these aspects will be described in the specific application of simulating the implantation of a micro-pacemaker small enough to be delivered with minimally invasive techniques through a catheter, and implanted directly into the heart. In one example, the micro-pacemaker is provided with flexible tines attachable to the interior of the right ventricle. The tines can be engaged and disengaged during the implantation process without causing trauma to the cardiac tissue, thereby allowing the device to be repositioned during implantation or retrieved if needed.

The various aspects of the present disclosure described therein are particularly well suited for training medical professionals to perform such transcatheter pacemaker implantation process although the skilled person in the art will appreciate that various other applications not limited to the medical field may also be envisaged.

Transcatheter pacemaker implantations are generally performed through an opening realized in the femoral artery in the groin region although other entry points may be used.

Training of such a procedure may be done as a sequence of procedures, for example an initial catheter insertion up to the heart, fine manipulation of the implant inside the heart before final attachment, or as complete procedure encompassing all the manipulations required for a complete implantation process.

The present apparatus thus allows training medical professionals on a sequence of procedures of the complete procedure with improved realistic feedback feeling.

The apparatus may be used with a conventional portable PC and is compact enough to provide a complete portable simulator fitting in a conventional carry-on luggage, as detailed below.

Figure 1:
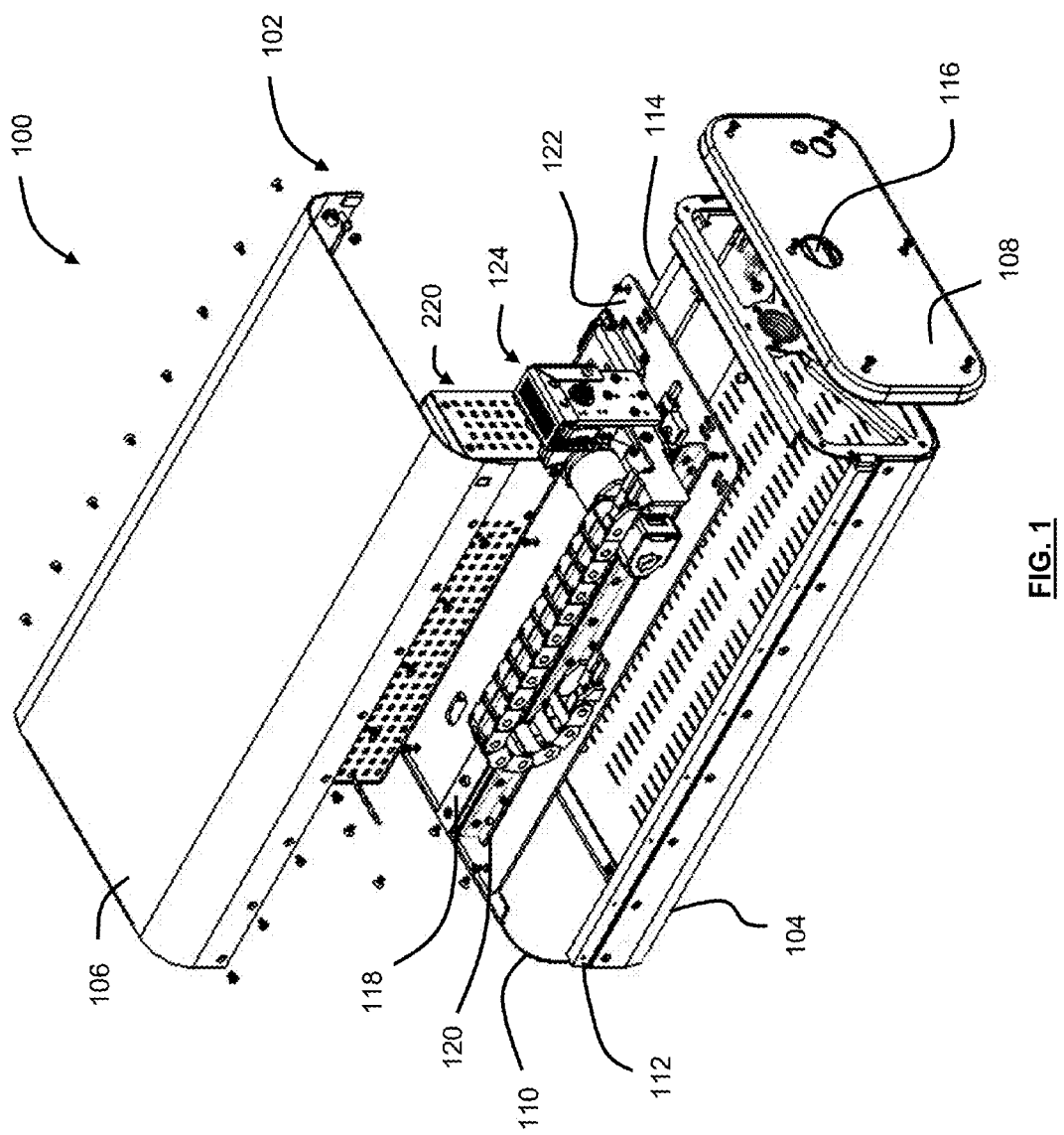
FIG. 1 is a partially exploded perspective view of an example of an apparatus for simulating insertion of an elongated instrument.

Referring to FIG. 1, there is shown a partially exploded view of an example of an apparatus 100 for simulating insertion of an elongated instrument (not shown), a medical catheter for example, into a structure such as an artery.

In the illustrated embodiment, the apparatus 100 has a casing 102 provided with bottom, top, front and back panels 104, 106, 108, 110 mounted together. The top panel 106 can be slidably mounted to the bottom panel 104 through slides 112, 114 mounted on the longitudinal sides of the panels 106, 104 for easing access to the interior of the casing 102 and enabling a quick installation of the elongated instrument in the apparatus 100.

The front panel 108 is provided with an aperture 116 for receiving a distal end of the elongated instrument therethrough, as it will become more apparent below with reference to FIGS. 8 to 12. Various additional apertures are provided, for example in the front and back panels, for power and electronics communication.

Figure 2:
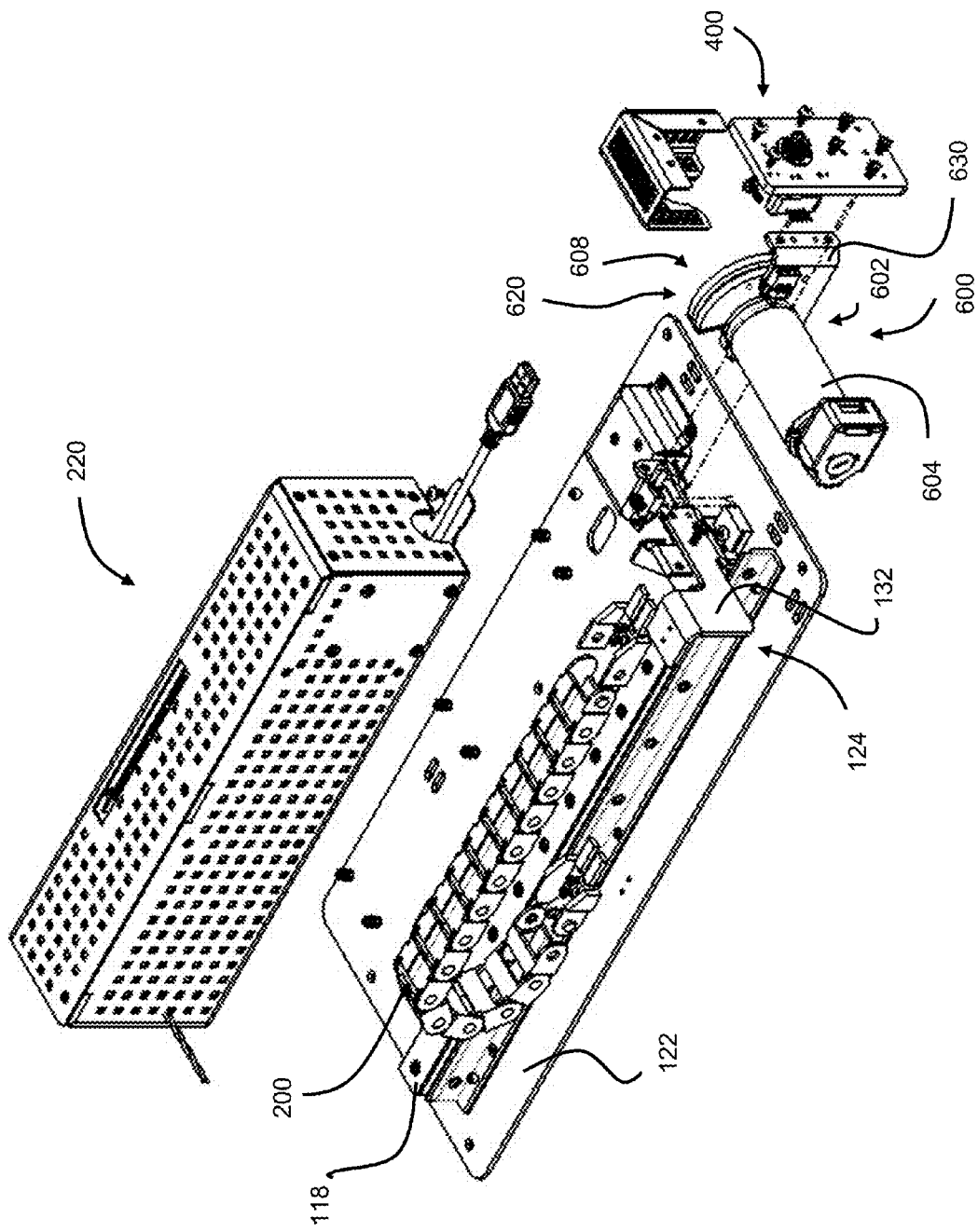
FIG. 2 is a further partially exploded perspective view of a portion of the apparatus of FIG. 1.
Figure 3:
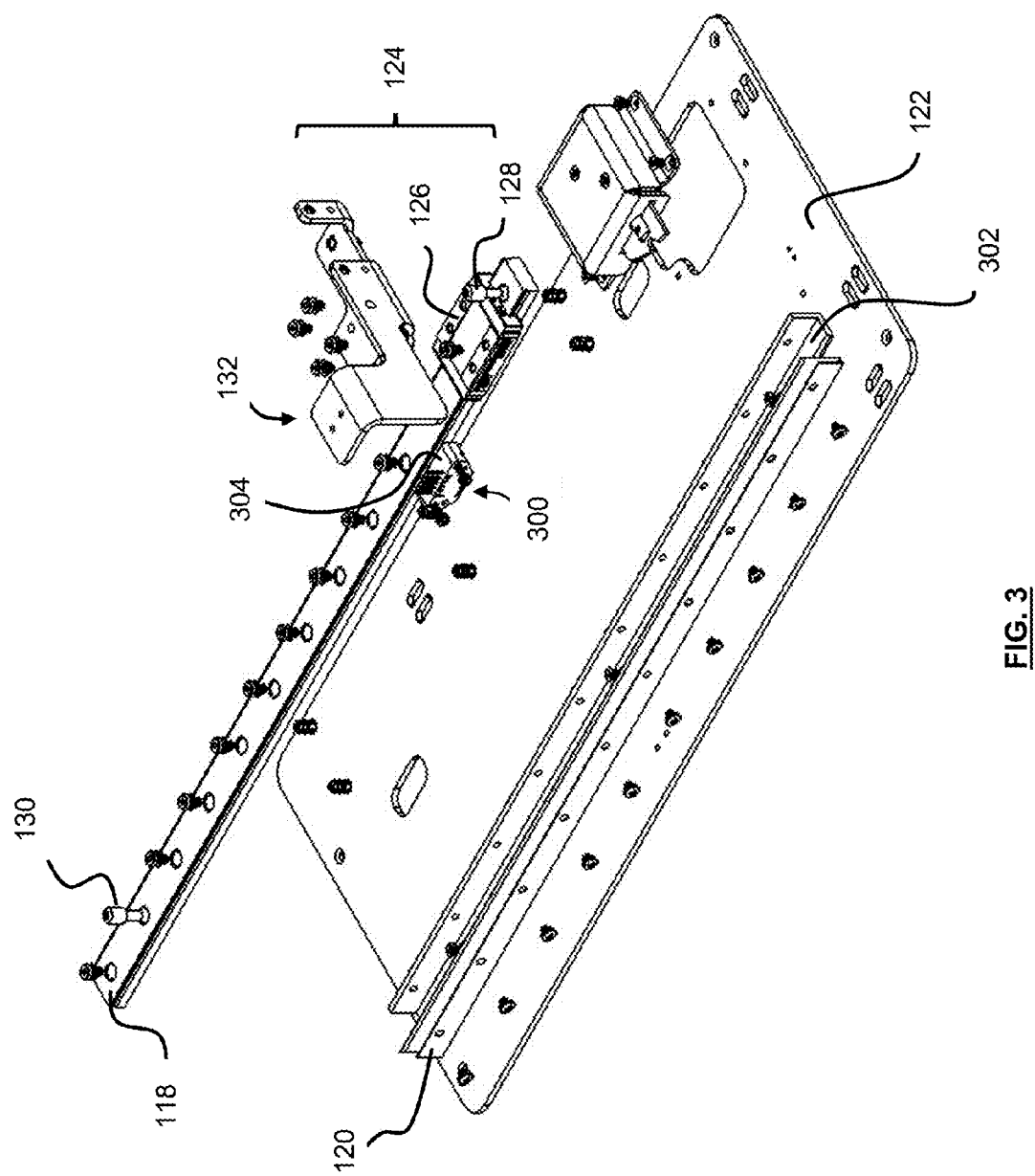
FIG. 3 is a further partially exploded perspective view of another portion of the apparatus of FIG. 1.

Still referring to FIG. 1 and also to FIG. 2 and FIG. 3 which are further exploded view of portions of the apparatus 100, the apparatus 100 is also provided with a longitudinal guide 118 fixedly mounted in the casing 102, for example through a guide rail 120 secured to a bottom mounting plate 122 secured to the bottom panel 104. The longitudinal guide 118 could consist of a rail, a pair of rails, a channel, a tunnel, or any other type of structure, which can act as a longitudinal guide. The apparatus 100 also has a carriage 124 slidably mounted onto the longitudinal guide 118 for translation therealong. In the illustrated embodiment, the carriage 124 has a base plate 126 freely sliding onto the guide 118 between two abutting positions defined with abutting elements 128, 130 mounted on each end on the guide 118 to restrain the travel of the carriage 124 onto a longitudinal operating range. Limits switches (not shown) can be provided for control purposes. The carriage 124 further has a mounting bracket 132 secured to the base plate 126 and a mounting plate 400 secured to the carriage 124 through the mounting bracket 132.

Figure 4:
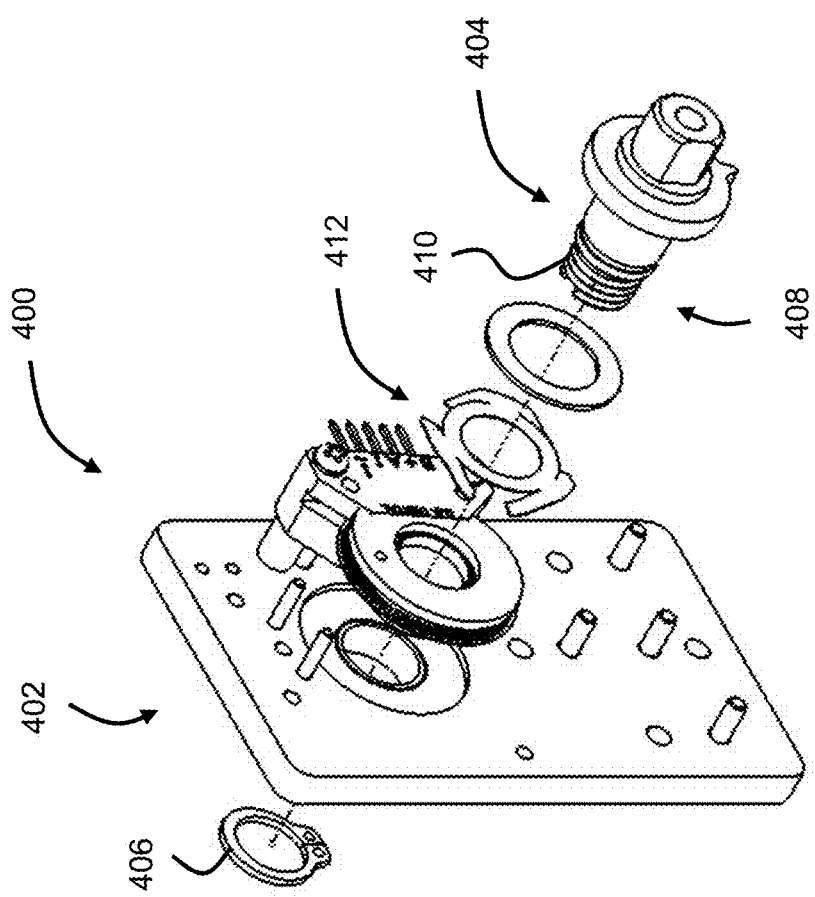
FIG. 4 is an exploded perspective view of a mounting plate and a mounting shaft arrangement.
Figure 5:
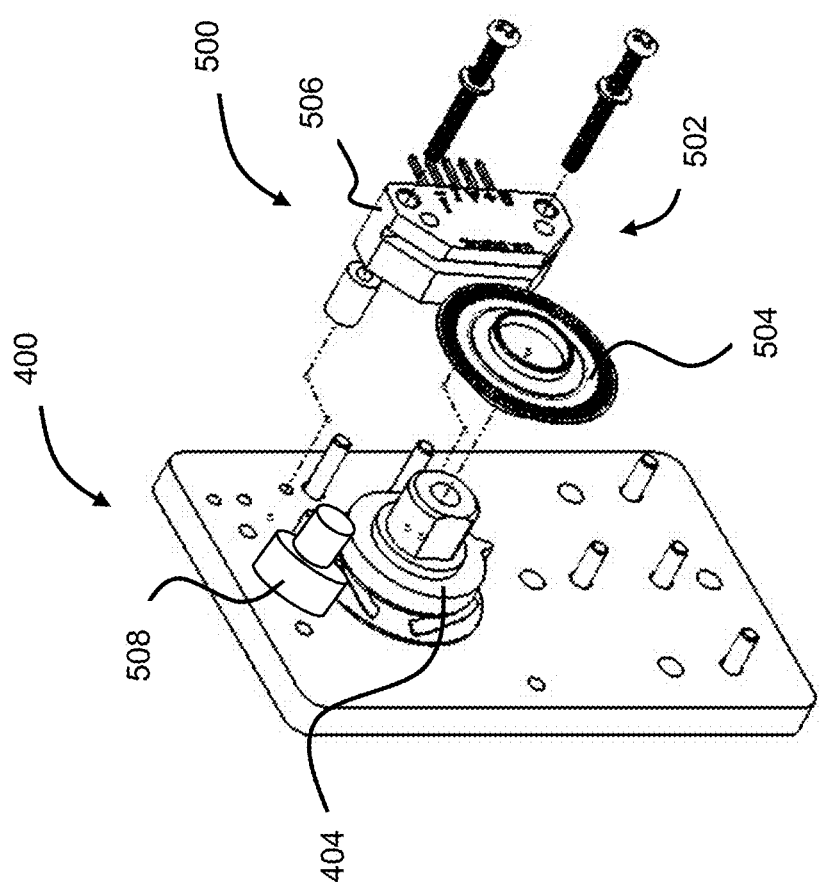
FIG. 5 is a partially exploded perspective view of the mounting plate of FIG. 4 with a sensing element.

The mounting plate 400, which is better shown in exploded views thereof in FIG. 4 and FIG. 5, is used for mounting the distal end of the elongated instrument to the carriage 124. With this arrangement, a translation of the elongated instrument operated by a user through the aperture 116 of the casing 102 for simulating insertion and/or removal of the elongated instrument will generate a corresponding translation of the carriage 124 along the longitudinal guide 118 inside the casing 102.

The mounting plate 400 has a receiving portion 402 for receiving a corresponding attaching portion (not shown) mounted at the distal end of the instrument. In the illustrated example, a shaft 404 is rotatably mounted through the mounting plate 400 and secured in place with snap ring 406 to thereby provide a axial rotating connection of the elongated instrument to the carriage 124. The tip 408 of the shaft 404 projecting outward the casing 102 has a threaded portion 410 for receiving a corresponding threaded portion of the distal end of the instrument to firmly secure the two elements together. An optional rotation stopper 412 may be installed with the shaft 404 to limit the axial rotational course of the shaft 404 to thereby limit the axial rotational course of the elongated instrument through the aperture 116 of the casing 102.

To provide a more realistic feedback to a user of the apparatus 100, a feedback system sensitive to the axial rotation of the instrument is provided. As illustrated, an angular position sensing element 500 can be used for sensing a relative axial rotation of the shaft 404 and thereby of the elongated instrument. The angular position sensing element 500 can be for example an optical encoder 502 having a circular disk 504 fixedly mounting around the shaft 404 and an associated optical reader 506 secured to the mounting plate 400. An angular feedback force actuator 508 mounted with the mounting plate 400 may be used for applying an adjustable resistive force to a rotation of the shaft 404 according to the sensed relative axial rotation, as further detailed below.

Referring again to FIG. 2, the apparatus 100 is provided with a feedback force actuator 600 mounted on the carriage 124 applying resistive force to a translation of the carriage 124 on the longitudinal guide 118. In the illustrated embodiment, the feedback force actuator 600 has an electric motor 602 (for example a stepper motor) whose frame 604 is secured to the carriage 124 though a mounting plate 630 secured to the mounting plate 400. The feedback force actuator 600 may optionally further comprise a transmission element 200 mounted between the motor 602 and the guide 118 for applying a resistive force to the carriage 124. The transmission element 200 could consist of a belt cooperating with the rotating shaft 608 of the motor 602 although various other arrangements for applying a resistive force to the carriage 124 may alternatively be envisaged.

A carriage position sensing element 300, a linear encoder strip 302 mounted along the guide 118 and a corresponding optical reader 304 as shown in FIG. 3 for example, is used for sensing a longitudinal position of the carriage 124 along the longitudinal guide 118.

The apparatus 100 is provided with an embedded control unit 220 mounted on the bottom plate 122 for controlling the feedback force actuator 600 according to the sensed position of the carriage 124 and eventually the sensed relative axial rotation of the elongated instrument, and further according to resistance characteristics of the structure. The resistance characteristics of the structure are representative of a patient's internal structure into which a medical catheter is to be inserted. These resistance characteristics may be provided by a specific 3D model of a structure of a specific patient and may embed natural movements of a human body like heart beating and breathing.

Figure 12:
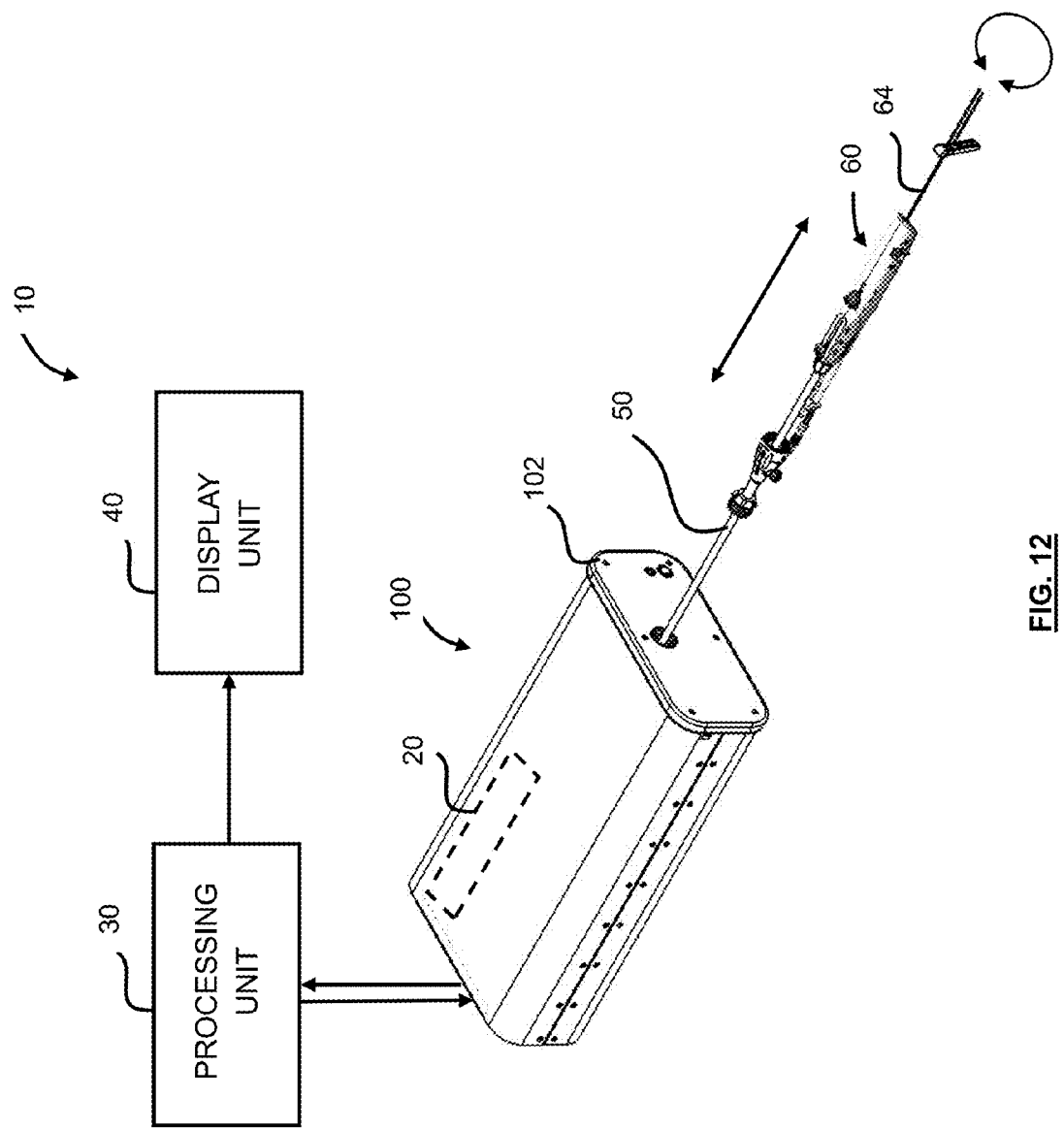
FIG. 12 is a schematic view of an example of a medical insertion simulator.

With reference to FIG. 12, a medical insertion simulator 10 will now be described. The medical insertion simulator 10 is provided with an apparatus 100 for simulating insertion of an elongated instrument into a structure as described above and shown in FIG. 1 and a corresponding elongated instrument 50 for attachment in the apparatus 100. The medical insertion simulator 10 also has a control unit 20 embedded in the casing 102 of the apparatus 100 for controlling the feedback force actuator 600.

The medical insertion simulator 10 is further provided with a processing unit 30 connected to the apparatus 100 for receiving the sensed longitudinal position of the carriage 124 and eventually the sensed relative axial rotation of the elongated instrument 50. At least one model of a patient's internal structure and associated resistance characteristics of the structure is provided to the processing unit 30 for further determination of the adjustable resistive force to apply to the translation of the carriage 124 and eventually the adjustable resistive force to apply to the relative axial rotation of the elongated instrument 50 according to previously received position information. The processing unit 30 further operates the control unit 20 to simulate a realistic insertion in the specific structure in providing forces (i.e. haptic feedback) to the movements of the user operating the elongated instrument 50. The processing unit 30 further produces a visual display image of the patient's internal structure and movement of the elongated instrument 50 therein and displays the produced visual display image in real time on a display unit 40. The processing unit 30 can be for example a portable computer provided with suitable control cards and software.

Figure 11:
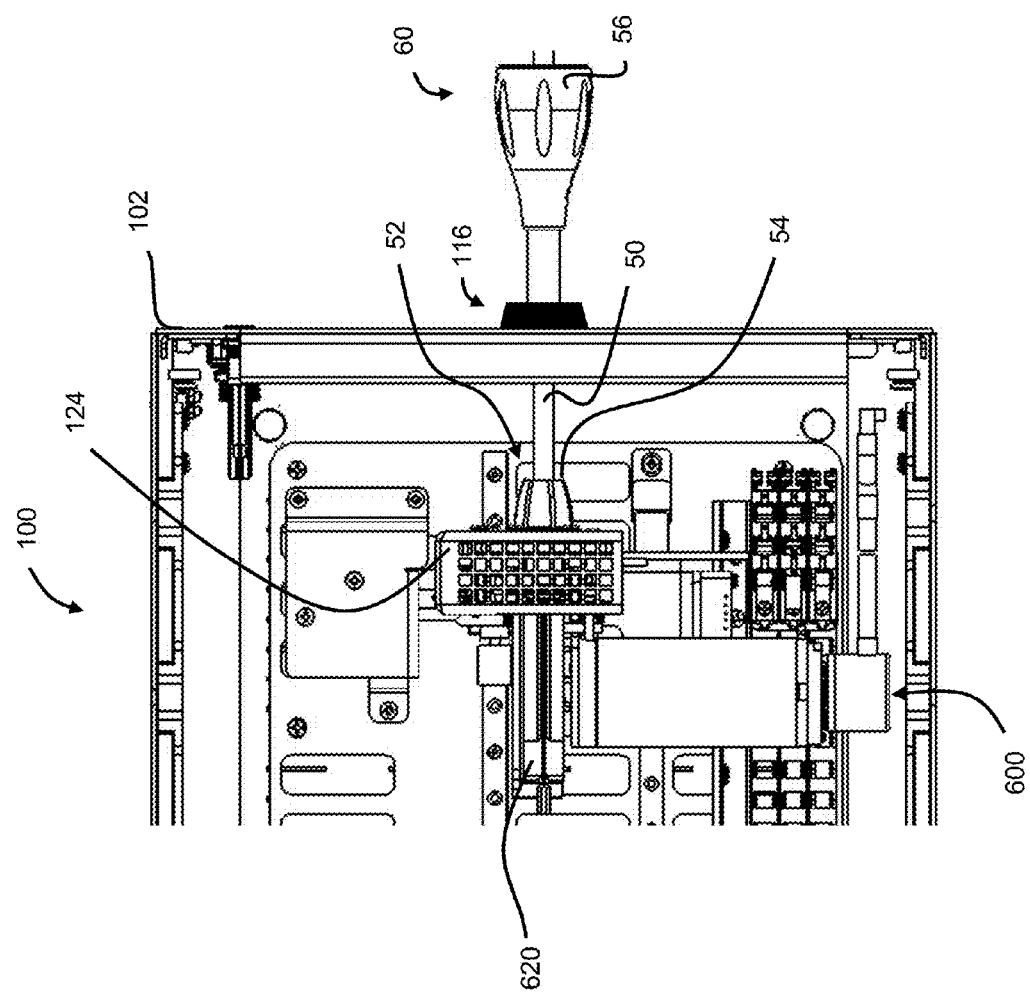
FIG. 11 is a top view of a portion of the apparatus of FIG. 7, with an elongated instrument mounted therein.
Figure 13:
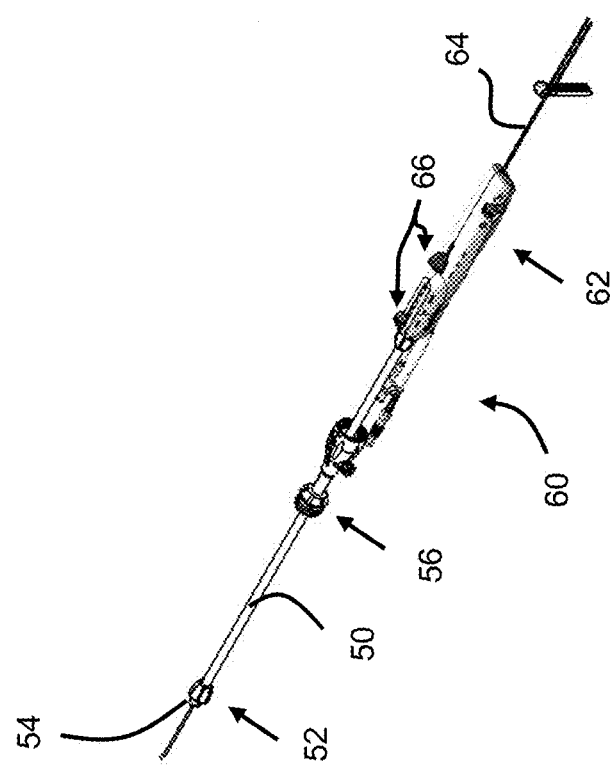
FIG. 13 is a perspective view of an example of an elongated instrument.

Reference is now made to FIG. 13 showing an example of a training handle 60 usable with the apparatus 100 and to FIG. 11. The training handle 60 has a gripping portion 62 connected to a rigid elongated instrument 50 connectable to the mounting plate 400. The distal end 52 of the rigid elongated instrument 50 is provided with a threaded tip 54 for mounting with the threaded portion 410 of the tip 408 of the shaft 404. Optionally, an introducer 56 may be coaxially secured with the rigid elongated instrument 50 in the aperture 116 of the casing 102 to provide a sliding longitudinal relationship of the training handle 60 in and out of the casing 102.

In the illustrated example, the training handle 60 is further provided with a tether 64 extending through the rigid elongated instrument 50 and the gripping portion 62 and therealong. The distal end of the tether 64 (which corresponds to the distal end 52 of the rigid elongated instrument 50) is used to simulate the position of a medical implantable device to which the tether 64 is attached. The tether 64 is driven inside and out of the rigid elongated instrument 50 through controls 66 provided on the gripping portion 62. The controls 66 further allow controlling the distal end 52 of the rigid elongated instrument 50. Additional controls for simulating further spatial movements of the medical implantable device attached to the tether 64 may also be provided for further realistic simulation of a complete implantation procedure, as it will become apparent below.

Figure 6:
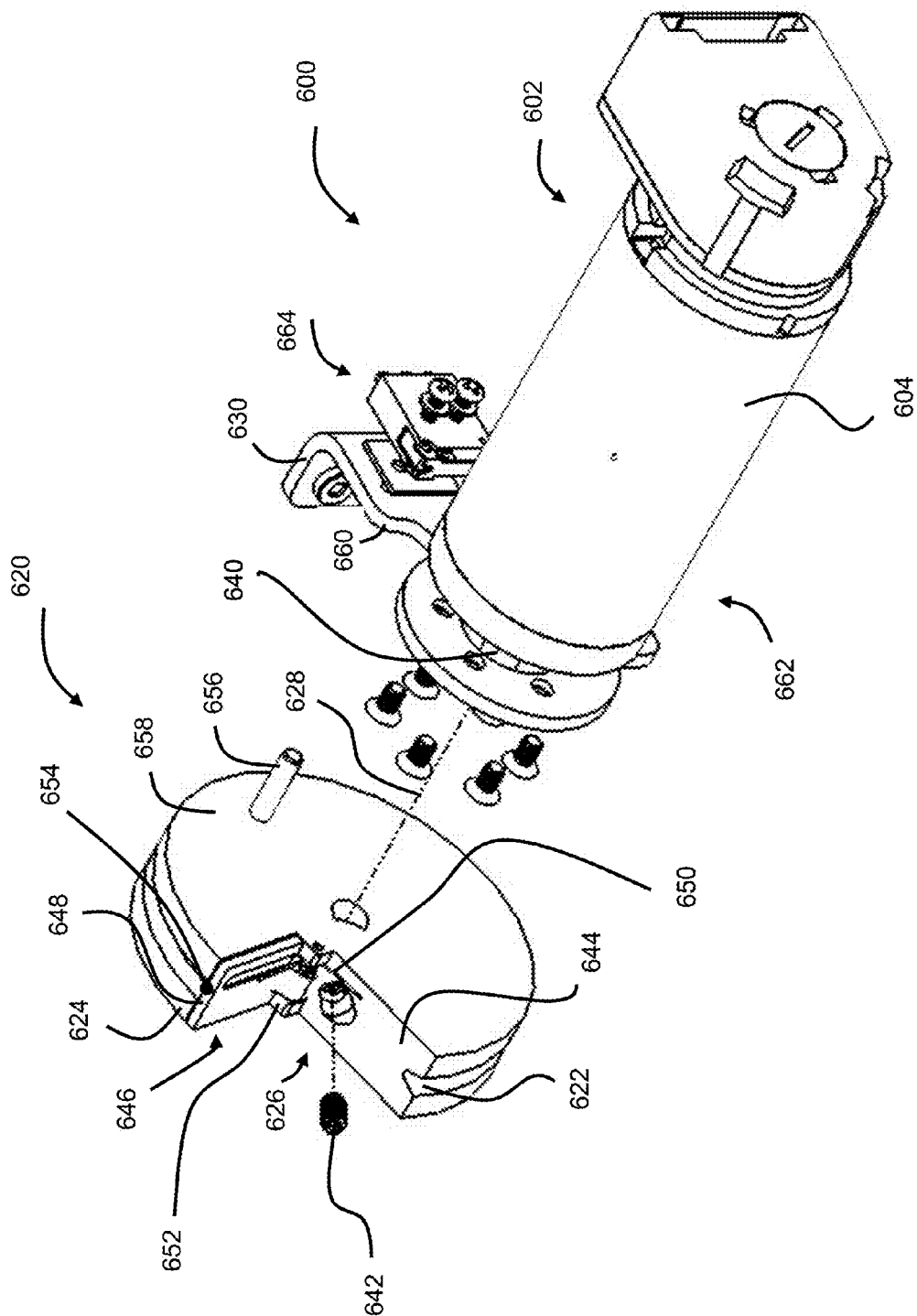
FIG. 6 is an exploded view of a pulley and a feedback force actuator of the apparatus of FIG. 1.

Referring again to FIG. 1 and FIG. 2 and also to FIG. 6 which is an exploded view of a portion of the apparatus shown in FIG. 1, the apparatus 100 may also be used for simulating insertion of an elongated instrument, for example a medical implantable device, attached to a tether into a structure, for example a patient's internal structure into which the medical implantable device is to be implanted. In other words, this arrangement may enable to simulate installation of the medical implantable device into the structure once this implantable device has already been brought proximate the structure into which the implantation has to be performed.

The aperture 116 of the casing 102 receives a distal end of the tether therethrough for attachment therein, as better described below with reference to FIG. 10. The apparatus 100 is provided with a pulley 620 having an outer tether receiving groove 622 on a peripheral portion 624 thereof and an anchoring element 626 therein for anchoring the distal end of the tether extending through the aperture 116 of the casing 102. The pulley 620 is rotatably mounted in the casing 102 for rotating according to a longitudinal translation of the tether relatively to the casing 102.

The apparatus 100 also has a feedback force actuator 600 connected to an axle 628 of the pulley 620 for applying an adjustable resistive force to a rotation of the pulley 620. As better shown in FIG. 6, the feedback force actuator 600 is for example an electric motor 602, such as for example a stepper motor, operatively connected to the axle 628 of the pulley 620. In the illustrated example, the stepper motor 602 is operatively connected to the casing 102 through a mounting plate 630 attached to the frame 604 of the motor 602. The shaft 640 of the motor 602 is mounted on the axle 628 of the pulley 620 and is secured in place through a set screw 642 extending radially to the axle 628 through the pulley 620. In the illustrated example, the pulley 620 has the shape of a partial disk or a disk in which a radial portion has been removed to provide opposed radial surfaces 644, 646. The set screw 642 is mounted with the axle through one of the radial surfaces. A retaining plate 648 associated with a torsion spring 650 and a pin spring 652 is arranged between the two radial surfaces 644, 646 to retain the retaining plate 648 against a corresponding radial surface. This arrangement defines an anchoring point 654 for anchoring the distal end of the tether to the pulley 620 while a portion of the tether extends in the outer tether receiving groove 622 on the peripheral portion 624 of the pulley 620. With this arrangement, the tether can be easily installed and removed from the apparatus 100.

Still referring to FIG. 6, the pulley 620 may be provided with an abutting pin 656 extending radially on the side 658 of the pulley 620 and cooperating with an associated abutting device attached to the casing 102 for restraining a pivotal movement of the pulley 620. As illustrated, the mounting plate 630 used for mounting the motor 602 may be shaped to provide an abutting shaped surface limiting the rational course of the pulley 620. As an example, the mounting plate 630 has a circular portion around which the abutting pin 656 may freely moves and two abutting elements 660, 662 projecting radially for defining two abutting positions. Various alternative arrangements may be envisaged for restraining movement of the pulley 620.

The apparatus 100 is also provided with a sensing arrangement 664 for sensing an angular position of the pulley 620. The sensing arrangement 664 has a sensor mounted to the mounting plate 630 for sensing a relative position of the abutting pin 656. Alternatively, as it should become apparent below, the relative position of the tether tip could be determined through the controls provided on a training handle.

Figure 8:
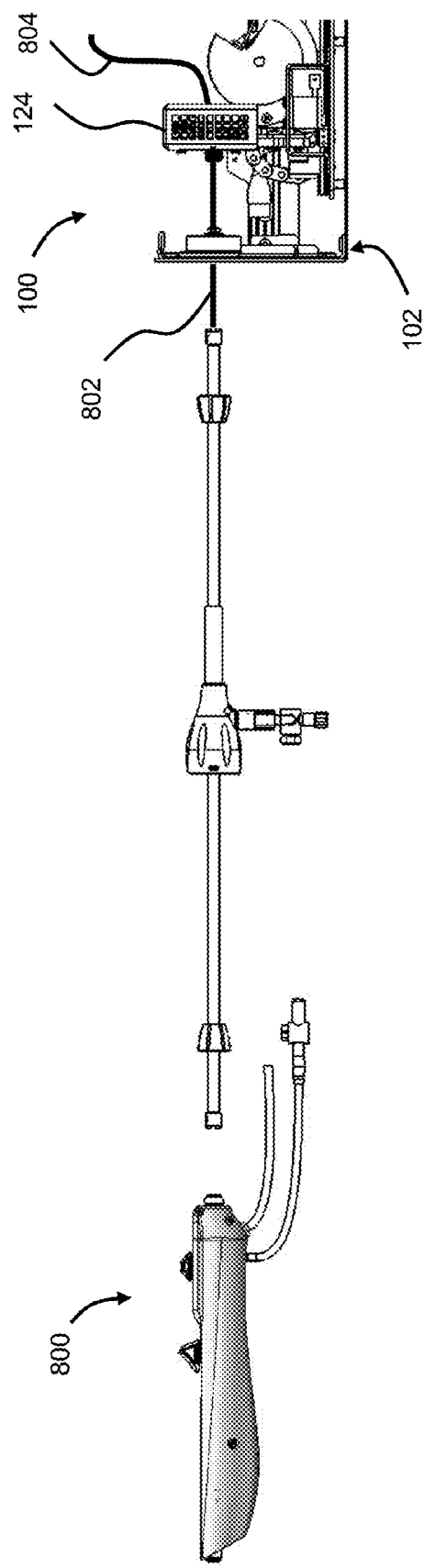
FIG. 8 is an exploded partial side view of the apparatus shown in FIG. 7.
Figure 9:
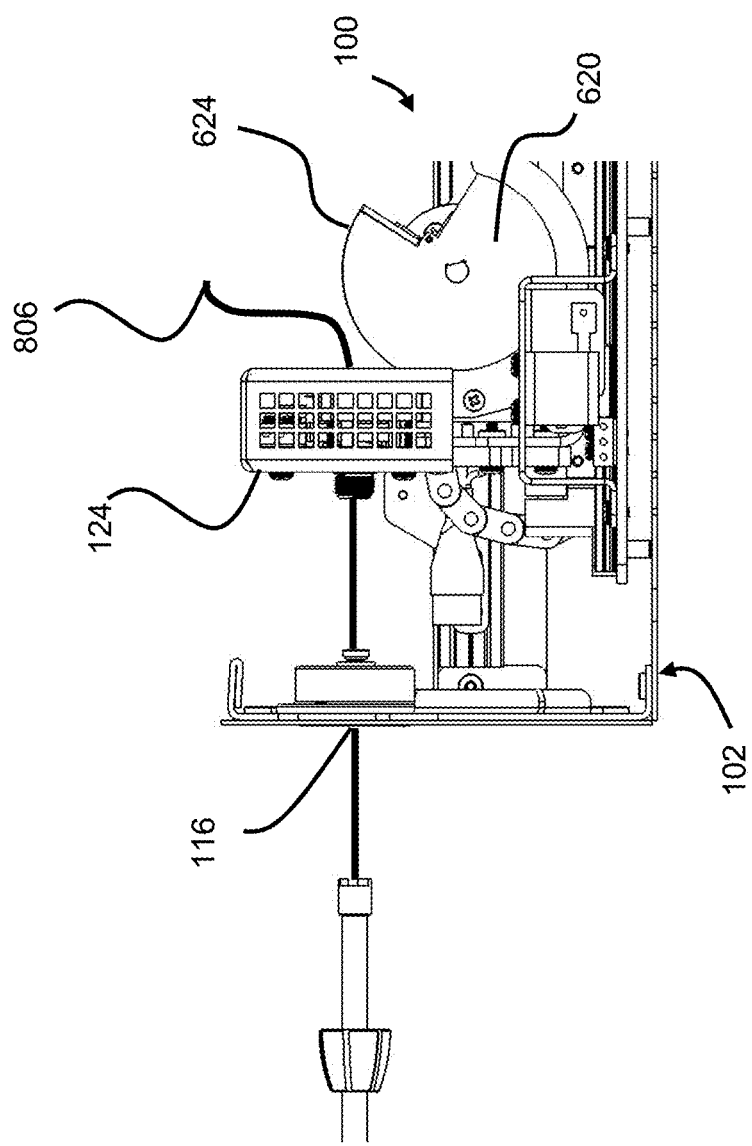
FIG. 9 is an enlarged view of the right portion of FIG. 8.
Figure 10:
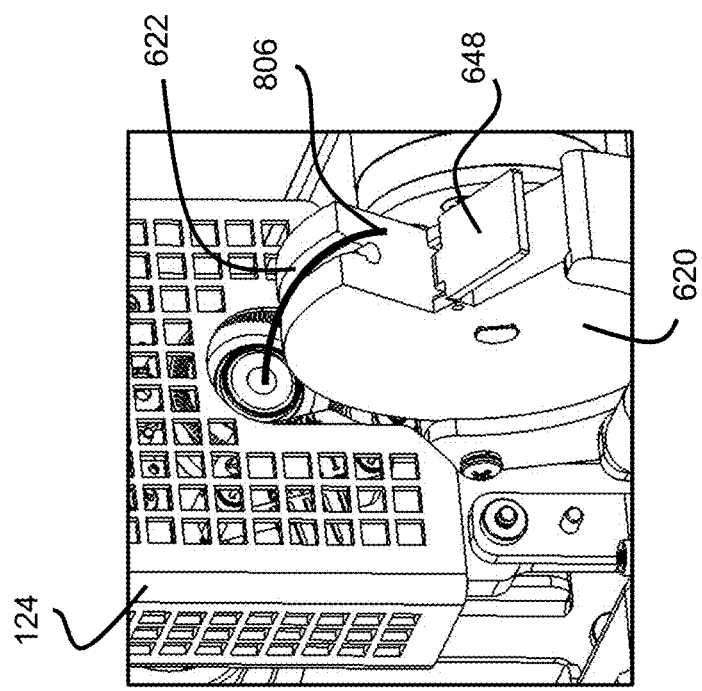
FIG. 10 is a perspective partial view showing the mounting of a tether with a pulley.

In addition to FIG. 6, reference is now made to FIG. 8 to FIG. 10 which are partial views of the apparatus 100 showing the anchoring of the distal end of the tether to the pulley 620. In the illustrated example, a training handle 800 similar to the one illustrated in FIG. 13 and provided with a tether 802 is used. The distal end 804 of the tether 802, which can be provided with a tip 806 having a larger diameter than the outer tether receiving groove 622 of the pulley 620, is first inserted through the aperture 116 of the casing 102. To attach the distal end 804 of the tether 802 to the pulley 620, one has first to rotate the retaining plate 648 (see FIG. 10), insert the tip 806 of the distal end 804 in the outer tether receiving groove 622 on the peripheral portion 624 and trap this end 804 with the pulley 620 in releasing the spring biased retaining plate 648.

As it should become apparent, upon longitudinal translation of the tether 802 inside the casing 102, the pulley 620 rotates while the tether 802 freely winds in the receiving groove portion 622. The sensed angular position of the pulley 620 is representative of a relative longitudinal position of the tip 806 of the tether 802 in the casing 102.

The apparatus 100 is provided with an embedded control unit 220 mounted on the bottom plate 122 for controlling the feedback force actuator 600 according to the sensed angular position of the pulley 620, and further according to resistance characteristics of the structure. The resistance characteristics of the structure are representative of a patient's internal structure into which an elongated instrument like a medical implantable device is to be inserted. These resistance characteristics may be generated using a 3D model of a structure of a specific patient, embedding natural movements of a human body like heart beating and breathing. The resistance characteristics may comprise a combination of predetermined resistance characteristics (i.e. static) and modeled resistance characteristics (i.e. dynamic).

The assembly of the pulley 620 and the actuator 600 may be fixedly mounted in the casing 102. Alternatively and as illustrated in FIG. 1 to FIG. 3, the pulley 620 may be mounted on the carriage 124 slidable along the longitudinal guide 118. This latter arrangement may provide a more realistic simulation of an installation of a medical implantable device into a structure embedding natural movements of a human body.

Referring again to FIG. 12, another example of a medical insertion simulator 10 for simulating an installation of a medical implantable device into a structure will now be described. The medical insertion simulator 10 is provided with an apparatus 100 for simulating insertion of an elongated instrument, such as a medical implantable device, attached to a tether, into a structure, the apparatus 100 having a pulley and feedback force actuator assembly 620, 600 just previously described and shown in FIG. 6. The medical insertion simulator 10 is also provided with a tether 64 embedded in a training handle 60. The tether 64 has a distal end for anchoring to the anchoring element of the pulley 620. The medical insertion simulator 10 also has a control unit 20 embedded in the casing of the apparatus 100 for controlling the feedback force actuator 600 of the pulley 620.

The insertion simulator 10 is further provided with a processing unit 30 connected to the apparatus 100 for receiving the sensed angular position of the pulley 620. At least one model of a patient's internal structure and associated resistance characteristics of the structure is provided to the processing unit 30 for further determination of the adjustable resistive force to apply to the rotation of the pulley 620 according to previously received position information. The processing unit 30 further operates the control unit 20 to simulate a realistic implantation in the specific structure in providing forces to the movements of the user operating the tether 64. The processing unit 30 further produces a visual display image of the patient's internal structure and movement of the implantable device therein and displays the produced visual display image in real time on a display unit 40.

As it should be apparent, the apparatus for simulating insertion and associated simulators previously described enable a realistic medical training of the initial catheter insertion up to the heart only, or the fine manipulation only of the implantable device inside the heart structure before final attachment thereto.

Referring again to FIG. 1 and FIG. 2 and also to FIG. 12, another example of an apparatus 100 and associated simulator 10 enabling to simulate the whole implantation procedure including initial catheter insertion up to the heart and subsequent fine manipulation of the implantable device outside the catheter for final attachment will now be described. This apparatus 10 controls whole or partial simulation. In the following description and for ease of understanding, in which the catheter used to bring the implantable device up to the structure is alternatively called the outer elongated instrument while the implantable device initially extending inside the catheter and attached to a tether is called the inner elongated instrument.

The apparatus 10 has a casing 102 having an aperture 116 for receiving a distal end of the outer elongated instrument therethrough and a longitudinal guide 118 fixedly mounted in the casing 102. The apparatus 100 also has a carriage 124 provided with a mounting plate 400 for mounting the distal end of the outer elongated instrument. The carriage 124 is slidably mounted onto the longitudinal guide 118 for translation thereon according to a translation of the outer elongated instrument through the aperture 116 of the casing 102, as previously detailed. A carriage position sensing element 300 is provided for sensing a longitudinal position of the carriage 124 along the longitudinal guide 118. The apparatus 100 is also provided with a pulley 620 having an outer tether receiving groove 622 on a peripheral portion 624 thereof and an anchoring element 626 therein for anchoring a distal end of a tether extending through the outer elongated instrument. The pulley 620 is rotatably mounted on the carriage 124 for rotating according to pulling of the tether into the outer elongated instrument, as previously detailed. A pulley position sensing arrangement 664 is also provided for sensing an angular position of the pulley 620 representative of a relative longitudinal position of the inner elongated instrument attached to the tether. The apparatus 100 is also provided with a feedback force actuator 600 mounted on the carriage 124 and operatively connected to the casing 102 for applying an adjustable resistive force to a translation of the carriage 124 on the longitudinal guide 118 according to the sensed longitudinal position of the carriage 124 and resistance characteristics of the structure as previously detailed. The feedback force actuator 600 is further connected to an axle 628 of the pulley 620 for applying an adjustable resistive force to a rotation of the pulley according to the sensed angular position of the pulley 620 and the resistance characteristics of the structure. To provide a more realistic simulation, an axial rotation of the outer elongated instrument through the aperture 116 of the casing 102 may be sensed with an angular position sensing element 500 mounted on the mounting plate 400 of the carriage 124, while an angular feedback force actuator 508 is provided for applying an adjustable resistive force to such sensed axial rotation, according to the resistance characteristics of the structure. The apparatus 100 is provided with an embedded control unit 220 for controlling the feedback force actuators according to the various sensed positions.

The apparatus 100 previously described may be used in a medical insertion simulator as illustrated in FIG. 12.

In the illustrated examples, a single stepper motor 602 is controlled according to various modes of simulation for providing corresponding resistive forces to the pulley 620 and the carriage 124. This arrangement is of great advantage to provide a compact apparatus. Others arrangements for actuating the carriage 124 and the pulley 620 may also be envisaged, for example two distinct actuators suitably mounted and controlled.

Figure 7:
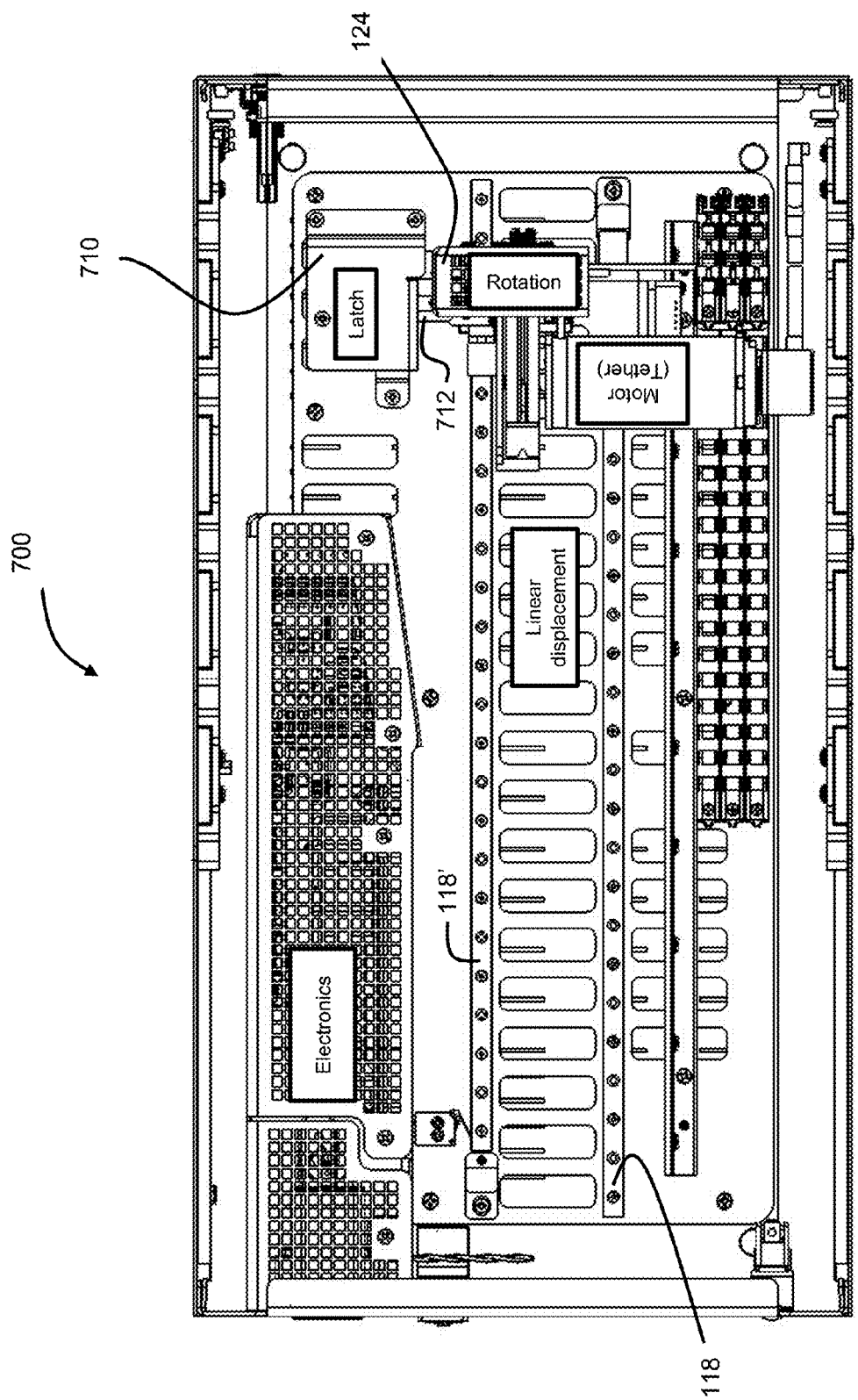
FIG. 7 is a top view of another example of an apparatus for simulating insertion of an elongated instrument.

FIG. 7 shows another embodiment of an apparatus 700 for simulation insertion wherein the arrangement used for applying the resistive force to the carriage 124 is slightly different. The carriage 124 is also mounted on two parallel longitudinal guides 118, 118'. A controlled latch mechanism 710 mounted to the casing 102 and having a movable member 712 cooperating with the carriage 124 is provided for latching the carriage 124 in resting position, for transport purposes and/or according to a specific simulation application for example.

With its embedded control unit and its compact design, the apparatus may be operated through a portable computer and associated control cards and software to provide a portable realistic simulator easy to mount and use. The apparatus may have a casing of a total weight of 10 lb with total dimensions small enough to fit with a portable computer and associated accessories in a carry-on whose dimensions are less than 25"×20"×14.5", which is of great advantage for transport purposes. In fact, the apparatus is designed small enough to fit in a carry-on while still providing an operating range long enough to enable a realistic simulation of an implantation of a medical implantable device in the heart through the femoral artery.

Although the present disclosure has been described hereinabove by way of non-restrictive, illustrative embodiments thereof, these embodiments may be modified at will within the scope of the appended claims without departing from the present claims.

What is claimed is:

1. An apparatus for simulating insertion of an inner elongated instrument attached to a tether into a structure through an outer elongated instrument, the apparatus comprising:
   a casing having an aperture for receiving the outer elongated instrument therethrough;
   a longitudinal guide fixedly mounted in the casing;
   a carriage comprising a mounting plate and a shaft rotationally mounted through the mounting plate, the shaft receiving a distal end of the outer elongated instrument, the carriage being slidably mounted onto the longitudinal guide for translation thereon according to a translation of the outer elongated instrument through the aperture of the casing;
   a carriage position sensing element for sensing a longitudinal position of the carriage along the longitudinal guide;
   a pulley having an outer tether receiving groove on a peripheral portion thereof and an anchoring element therein for anchoring a distal end of a tether extending through the outer elongated instrument, the pulley being rotatably mounted on the carriage for rotating in response to a pulling movement of the tether by a user of the outer elongated instrument in the outer elongated instrument;
   a pulley position sensing arrangement for sensing an angular position of the pulley representative of a relative longitudinal position of the inner elongated instrument attached to the tether; and
   a feedback force actuator mounted on the carriage for applying resistive force to a translation of the carriage on the longitudinal guide according to the sensed longitudinal position of the carriage, the feedback force actuator being further connected to an axle of the pulley for applying resistive force to a rotation of the pulley according to the sensed angular position of the pulley.

2. The apparatus of claim 1, further comprising an angular position sensing element mounted on the mounting plate of the carriage for sensing a relative axial rotation of the outer elongated instrument through the aperture of the casing.

3. The apparatus of claim 2, further comprising an angular feedback force actuator for applying resistive force to a rotation of the outer elongated instrument through the aperture of the casing according to the sensed relative axial rotation.

4. The apparatus of claim 1, further comprising a control unit for controlling the feedback force actuator and applying the corresponding resistive forces to the translation of the carriage and the rotation of the pulley.

5. The apparatus of claim 1, wherein the feedback force actuator comprises a stepper motor mounted on the carriage and connected to the axle of the pulley, the feedback force actuator further comprising a transmission element mounted between the motor and the guide for applying the resistive force to the carriage.

6. The apparatus of claim 1, wherein the outer elongated instrument comprises a medical catheter and the inner elongated instrument attached to the tether is a medical implantable device, and further wherein the resistance characteristics of the structure are representative of a patient's internal structure into which the outer elongated instrument is to be inserted before the medical implantable device is to be implanted.

7. A medical insertion simulator comprising:
   an apparatus for simulating insertion of an inner elongated instrument attached to a tether into a structure through an outer elongated instrument of claim 1;

an outer elongated instrument for attachment in the apparatus;

a control unit for controlling the feedback force actuator;

a processing unit for receiving the sensed longitudinal position of the carriage, the sensed angular position of the pulley and a model of a patient's internal structure and associated resistance characteristics, the processing unit further determining the resistive force to apply to the translation of the carriage and the resistive force to apply to the rotation of the pulley according to previously received information for operating the control unit, the processing unit further producing a visual display image of the patient's internal structure and movement of the inner and outer elongated instruments therein; and a display unit for displaying the produced visual display image.

8. A medical insertion simulator comprising:

an apparatus for simulating insertion of an inner elongated instrument attached to a tether into a structure through an outer elongated instrument of claim 3;

an outer elongated instrument for attachment in the apparatus;

a control unit for controlling the feedback force actuator;

a processing unit for receiving the sensed longitudinal position of the carriage, the sensed angular position of the pulley, the sensed relative axial rotation and a model of a patient's internal structure and associated resistance characteristics, the processing unit further determining the resistive force to apply to the translation of the carriage, the resistive force to apply to the rotation of the pulley and the force to apply to the relative axial rotation according to previously received information for operating the control unit, the processing unit further producing a visual display image of the patient's internal structure and movement of the inner and outer elongated instruments therein; and a display unit for displaying the produced visual display image.

\* \* \* \* \*